US007008227B2

(12) United States Patent
Carmichael et al.

(10) Patent No.: US 7,008,227 B2
(45) Date of Patent: Mar. 7, 2006

(54) SELF-DRILLING IMPLANT

(76) Inventors: Robert P. Carmichael, 17 Austin Terrace, Toronto (CA) M5R 1Y2; George K. B. Sandor, 12 Hill Crescent, Toronto (CA) M1M 1H9

( * ) Notice: Subject to any disclaimer, the term of this patent is extended or adjusted under 35 U.S.C. 154(b) by 161 days.

(21) Appl. No.: 10/086,860

(22) Filed: Mar. 4, 2002

(65) Prior Publication Data
US 2003/0165796 A1 Sep. 4, 2003

(51) Int. Cl.
*A61C 8/00* (2006.01)
(52) U.S. Cl. ...................................... 433/174
(58) Field of Classification Search ............... 433/174, 433/173, 175, 176; 606/73
See application file for complete search history.

(56) References Cited

U.S. PATENT DOCUMENTS

| 3,981,079 | A | | 9/1976 | Lenczycki | |
|---|---|---|---|---|---|
| 4,341,206 | A | | 7/1982 | Perrett et al. | |
| 4,863,383 | A | * | 9/1989 | Grafelmann | 433/174 |
| 5,061,181 | A | | 10/1991 | Niznick | |
| 5,078,607 | A | | 1/1992 | Niznick | |
| 5,246,369 | A | | 9/1993 | Poulmaire | |
| 5,312,256 | A | | 5/1994 | Scortecci | |
| 5,362,234 | A | | 11/1994 | Salazar et al. | |
| 5,435,723 | A | | 7/1995 | O'Brien | |
| 5,601,429 | A | | 2/1997 | Blacklock | |
| 5,727,943 | A | | 3/1998 | Beaty et al. | |
| 5,816,812 | A | | 10/1998 | Kownacki et al. | |
| 5,947,735 | A | | 9/1999 | Day | 433/174 |
| 6,018,095 | A | | 1/2000 | Lerch et al. | |
| 6,048,204 | A | | 4/2000 | Klardie et al. | |
| 6,053,733 | A | * | 4/2000 | Aspichueta et al. | 433/173 |
| 6,217,331 | B1 | * | 4/2001 | Rogers et al. | 433/173 |
| 6,220,860 | B1 | * | 4/2001 | Hansson | 433/173 |
| 6,398,785 | B1 | * | 6/2002 | Carchidi et al. | 606/73 |

FOREIGN PATENT DOCUMENTS

EP 0 458 258 A1 11/1991
WO WO 97/25939 7/1997

(Continued)

OTHER PUBLICATIONS

Abstract taken from The International Journal of Oral & Maxillofacial Implants, vol. 13, No. 2, 1998, pp. 289 through 290.

(Continued)

*Primary Examiner*—Melba N. Bumgarner
(74) *Attorney, Agent, or Firm*—Bereskin & Parr

(57) ABSTRACT

In accordance with the invention, a dental implant comprises a body portion and a head portion. The body portion includes a tip portion which is remote from the head portion, a lead thread portion adjacent the tip portion, an intermediate thread portion adjacent the lead thread portion and a distal thread portion which is adjacent to the head portion. The dental implant further includes a central bore within the head portion. There is a thread within the bore for receiving a dental prosthesis. The tip portion comprises at least one cutting edge for cutting bone as the implant is rotated. The body portion includes at least one flute. The flute has a first end adjacent to the at least one cutting edge for assisting removal of bone cuttings from the cutting edge. In a more preferred embodiment of the invention, the implant includes at least two cutting edges and at least two flutes. In a particularly preferred embodiment, the flutes extend distally toward the head portion, but terminate at the end of the intermediate portion so that the distal thread portion does not have any portion thereof containing a fluted surface.

19 Claims, 2 Drawing Sheets

FOREIGN PATENT DOCUMENTS

| WO | WO 00/21455 | 4/2000 |
| WO | WO 00/53117 | 9/2000 |
| WO | WO 02/24102 A1 | 3/2002 |

OTHER PUBLICATIONS

Article-A multicenter reprot on osseointegrated oral implants by T. Albrektsson, M.D., Ph,D. taken from Maxillofacial Prosthetics, Dental limplants from The Journal of Prosthetic Dentistry, pp. 75 through 84 Jul. 1988.

Article-Mandibular Alveolar Ridge Augmentation in the Dog Using Distraction Osteogenesis by Michael S. Block, Andrew Chang and Craig Crawfod—pp. 309 through 314, 1996.

ACE Dental Implant System Mini-Catalog Quality, Precision and Innovative Desigin for Greater Performance 1998.

ACE Dental Implant System—Osteodynamics 1998.

Article—Section III Basic Science and Pathology—The Tension-Stress Effect on the Genesis and Growth of Tissues: Part II. The Influence of the Rate and Frequency of Distraction—by Gavriil A. llizarov, 1989.

Article- Section III Basic Science and Pathology—The Tension-Stress Effect on the Genesis and Growth of Tissues: Part I. The Influence of Stability of Fixation and Soft-Tissue Preservation by Gavriil A. llizarov 1989.

* cited by examiner

SELF-DRILLING IMPLANT

FIELD OF THE INVENTION

The present invention relates to the field of dental prosthesis. Specifically, the invention relates to the field of dental implants.

BACKGROUND OF THE INVENTION

Osseointegration is defined clinically as the process whereby clinically asymptomatic rigid fixation of alloplastic materials is achieved and maintained in bone during functional loading. Typical dental implants, when osseointegrated in the upper or lower jaw, provide stable anchorage for dental prostheses. To achieve successful osseointegration, it is normally required that the implant and the bone tissue at the surgical site be brought into close proximity to one another. Over time, as long as the implant remains undisturbed, the implant becomes osseointegrated with the bone. Once the implant has been successfully osseointegrated, the prosthetic devices may then be attached to the implant using the implant as the stable foundation for the prosthesis.

Integration of implants typically involves close fitting of an implant into the surgical site. Integration of the implant into the surgical site is often assisted by various techniques to ensure osseointegration. These may include surface treatment intended to promote osseointegration at a micro level, as well as contouring the surface of the implant to help to achieve osseointegration at a more macro level. Many implants which have been used are provided with a threaded outer surface. The threads of the threaded outer surface act as an aid in the osseointegration procedure.

When placing such typical implants, the oral surgeon must create a suitable socket into which the implant will be placed. This involves drilling a suitable size hole in the host bone. The use of a single drill of the same diameter as the dental implant, at high speed, can lead to necrosis in the bone, and thus much less aggressive techniques for making a suitable hole are typically used. It is standard for an oral surgeon to use three to five successively larger drill sizes to make one final hole of a diameter large enough to accommodate a typical implant. The first drill makes a relatively small hole. Each successive drill has a slightly larger diameter thereby enlarging the bore of the hole to achieve a desired diameter. Once the hole has been enlarged to an acceptable diameter, a dental implant may then be inserted into the hole made in the bone. Such an implant will then rely solely on osseointegration at a micro level between the bone and the surface of the implant for successful integration. In order for such osseointegration to successfully occur, the implant must fit very closely and accurately into the hole drilled in the bone. Obtaining such a close fit is difficult given the variance of each successive drilling procedure due to wobble, etc.

Typically, after the hole has been drilled to a desired diameter, the oral surgeon performs a further step. This further step involves using a tap to cut a thread in the surface of the bore of the hole which has been made using the drills. This produces a screw thread extending helically, proximally into the bone. The term "proximal" will be used in this specification and claims with reference to the bone involved to be the direction or surface which is closest to the centre of the bone representing the surgical site, while the term "distal" will be used to describe the direction or surface which is remote from the centre of the bone. Thus, the tap will create a helical thread extending proximally into the bone.

After the bore of the hole has been subjected to the cutting action of the tap, then an implant having a threaded exterior surface with a thread matching the thread of the tap used, may be screwed into the hole. The surgical site may then be permitted to heal. Over time, the implant will become osseointegrated into the drilled and tapped bone.

Because a non-aggressive drilling and tapping action is required in order to avoid necrosis of bone at the surgical site, the drilling speeds are typically kept quite low, often as low as 15 revolutions per minute.

This extended procedure thus involves, typically, use of as many as five drills followed by a tap, all of which must be operated at relatively slow speeds. This means that the surgical procedure itself involves a plurality of steps, all of which are conducted at relatively slow speeds, which thus prolong the surgical procedure and decrease precision. In addition, the procedure involves use of many components including the set of drills as well as the tap.

SUMMARY OF THE INVENTION

In accordance with the invention, a dental implant comprises a body portion and a head portion. The body portion includes a tip portion which is remote from the head portion, a lead thread portion adjacent the tip portion, an intermediate thread portion adjacent the lead thread portion and a distal thread portion which is adjacent to the head portion. The dental implant further includes a central bore within the head portion. There is a thread within the bore for receiving a dental prosthesis. The tip portion comprises at least one cutting edge for cutting bone as the implant is rotated. The body portion includes at least one flute. The flute has a first end adjacent to the at least one cutting edge for assisting removal of bone cuttings from the cutting edge.

In a more preferred embodiment of the invention, the implant includes at least two cutting edges and at least two flutes. In a particularly preferred embodiment, the flutes extend distally toward the head portion, but terminate at the end of the intermediate portion so that the distal thread portion does not have any portion thereof containing a fluted surface.

DETAILED DESCRIPTION OF THE DRAWINGS

Figure 1:
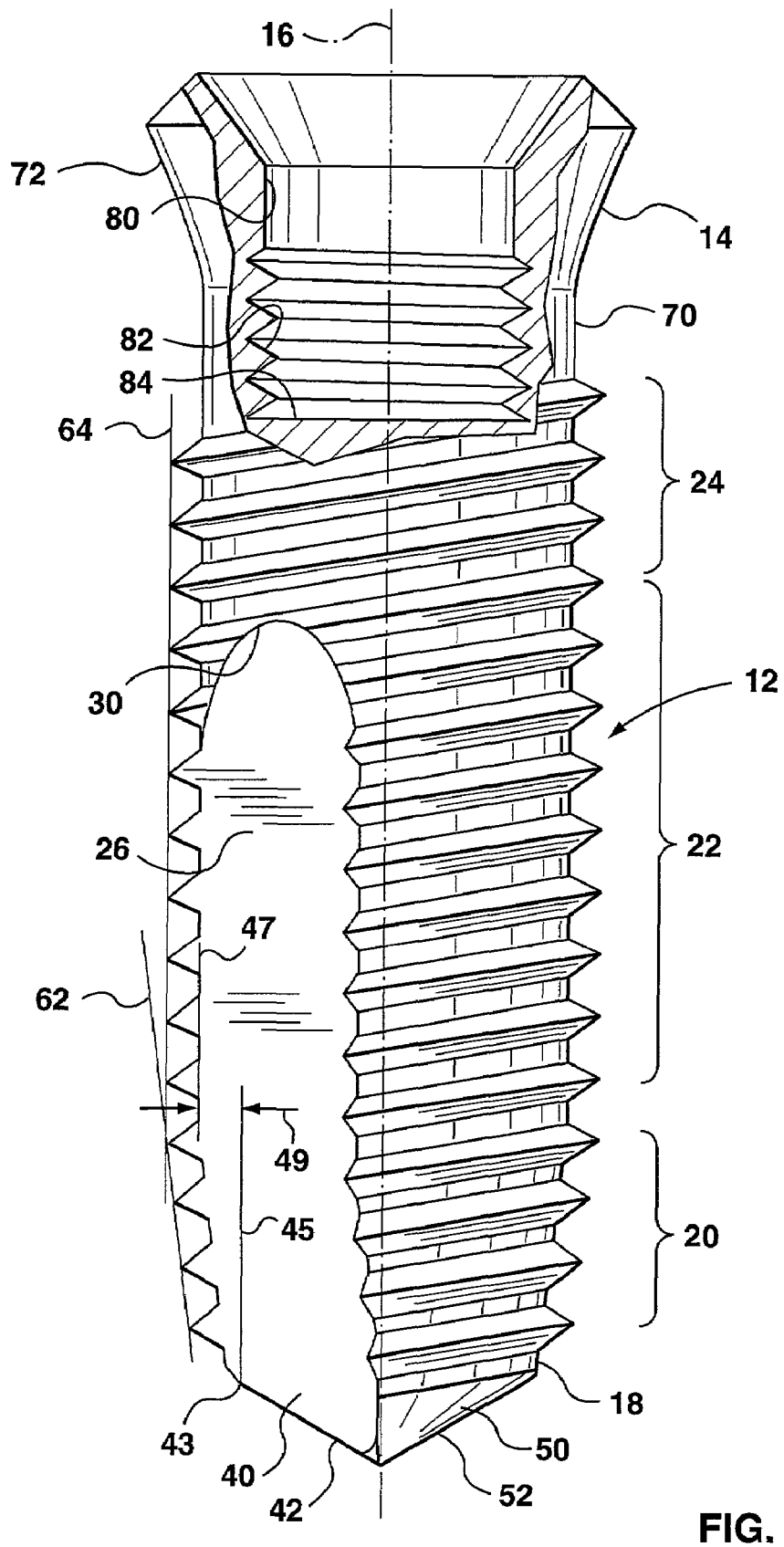
FIG. 1 is a side view of an embodiment of a dental implant in accordance with the present invention with a broken away sectional portion.

FIG. 1 illustrates a self-drilling dental implant 10. The implant 10 comprises a body portion 12 and a head portion 14. The implant 10 has a longitudinal axis 16 which extends from the head portion 14 to a tip portion 18 which is remote from the head portion 14. The body portion 12 comprises the tip portion 18, a lead thread portion 20, an intermediate thread portion 22 and a distal thread portion 24. The distal thread portion 24 is adjacent the head portion 14.

The body portion 12 comprises a pair of flute portions 26 and 28. The first flute portion 26 is visible in FIG. 1. The second flute portion 28 is partially visible in FIG. 2.

The pitch of the lead thread portion, the intermediate thread portion and the distal thread portion is the same so that as the implant is rotated, the thread will travel along a helical groove cut into the bone.

Figure 2:
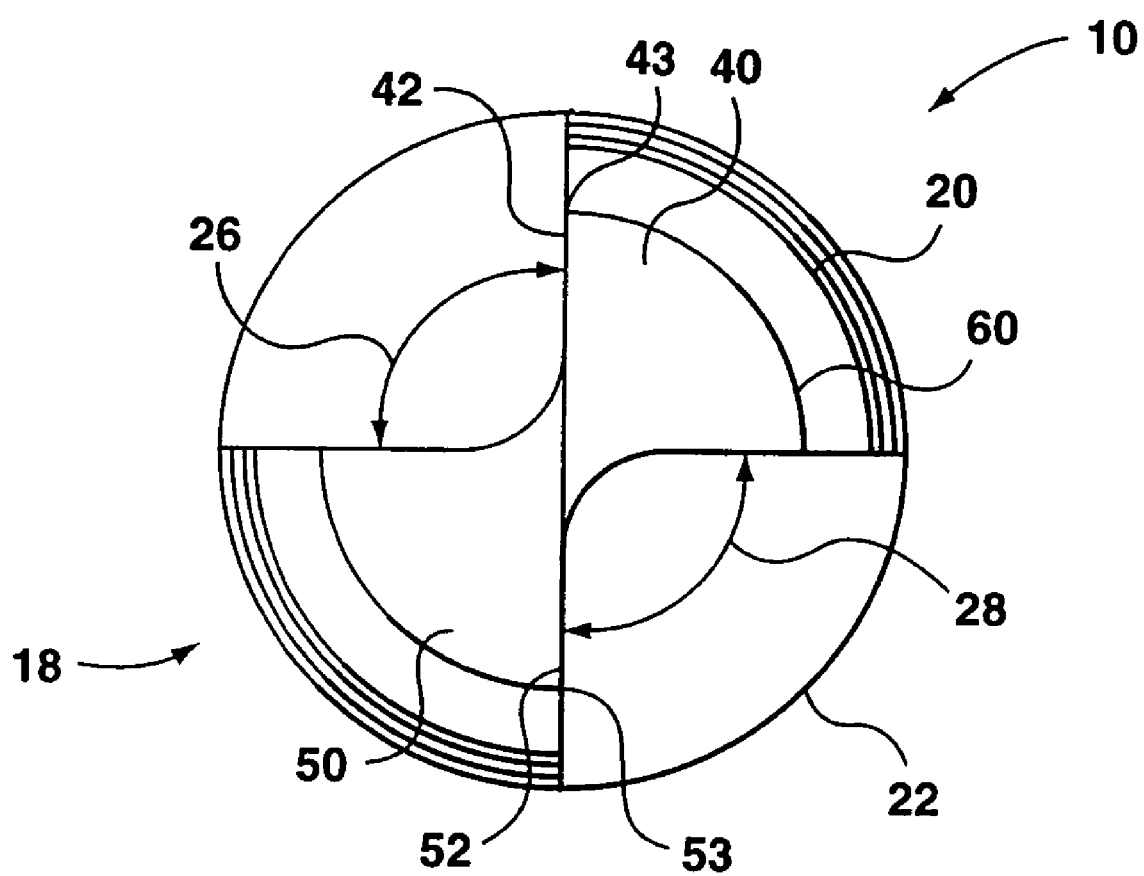
FIG. 2 is an end view of the implant of FIG. 1.

The tip portion 18 is most clearly shown in FIG. 2. The tip portion 18, includes a first cutting blade 40 and a second cutting blade 50. The first cutting blade 40 has a cutting edge 42 while the second cutting blade 50 has a cutting edge 52. One end of the first flute portion 26 is adjacent the cutting edge 42 of the first cutting blade 40, while one end of the second flute portion 28 is located adjacent the cutting edge 52 of the second cutting blade 50. The first cutting blade 40 and the second cutting blade 50 are arranged substantially symmetrically oppositely opposed about the longitudinal axis 16 and the cutting edges 42 and 52 extend outwardly from the longitudinal axis 16 to the distal end of the surface of the tip 18. The distal edge of the surface of the tip 18 is illustrated in FIG. 2 by the circle 60. The radially outer end of the cutting edges 42 and 52 is the point 43 and 53 respectively shown in FIG. 2.

As the implant 10 is rotated, when in place against the bone, the cutting edges 42 and 52 will cut bone from the host bone. The bone chips created by the cutting edges 42 and 52 flow into the first and second flute portions 26 and 28. From reference to FIG. 1, it will be observed that the flute portions, represent a relieved portion, cut into what is otherwise a substantially cylindrical threaded exterior surface of the implant 10. The flute portion 26 illustrated in FIG. 1 extends substantially parallel to the axis 16. Thus, bone chips created by the cutting edge 42 can flow in the distal direction along the flutes.

The implant 10 is a self-tapping and self drilling implant. Typically, when any type of device is said to be self-tapping, then the device must cut its way into the host site, in this case bone. Either the cut material must be compressed to allow the crest of the thread to pass through the bone, or bone material must be cut away permitting passage of the thread crest. In the case of a wood screw going into soft wood, the wood may be compressed on either side of the crest of the thread permitting the screw to advance into the wood and the crest of the thread to be received in the wood. Significant compression of this type is not acceptable in bone as this is likely to cause injury and in certain cases necrosis at the site of the thread crest. In order to not damage the surface of the bone which is immediately adjacent to the surface of the thread by compression, the cut material must be removed from the installation site. The cut material can be removed only by providing a path out of the installation site which does not generate significant compression of the host material. In the implant 10, the path for removal of bone cuttings is provided by the flute portions 26 and 28. In order to make that path as short as possible, the flute portions 26 and 28 extend substantially parallel to the axis 16. The flute portions 26 and 28 extend generally parallel to the axis 16 along the surface of the lead thread portion 20 and the intermediate thread portion 22. For reasons which will be discussed below, the flute portions 26 and 28 terminate at the end of the intermediate thread portion 22 and do not extend into the distal thread portion 24.

In order to install the implant 10, the surgical site may first be prepared for installation of the implant. The implant can be installed by directly engaging the soft tissue with the implant. In more typical situations, an incision will be made in the soft tissue. If desired a profiling drill may be used to create a dimple in the jaw bone at the desired location of the axis 16. This determines the location of the implant. The implant is then grasped in a tool to be discussed below at the head portion 14. Pressure in the proximal direction is applied to the implant 10 and the implant 10 is rotated. The cutting edges 42 and 52 then begin to remove bone chips from the host bone at the installation site. As the cutting edges create bone chips, the bone chips are forced to flow in the distal direction along the flute portions 26 and 28. The crest of the thread portions 20, 22 and 24 are also sharp so as to provide a cutting edge to facilitate the installation of the implant. The implant is rotated and advances in the proximal direction as the crest of the thread engages the cut host bone. The procedure is continued until the implant has been installed to the desired depth.

As the implant advances proximally, bone chips can flow into the flute portions 26 and 28 and out of the flute portions 26 and 28 while those flute portions extend distally above the distal surface of the host bone. The distal end 30 of the flute portion 26 is visible in FIG. 1. The second flute portion 28 also ends in a distal end which is located axially along the axis 16 adjacent to and diametrically opposite from the end 30.

As the implant nears its intended installation depth, the distal end 30 of the flute portion 26 will then be received in the host bone. As shown FIG. 1, the distal thread portion 24 comprises a few additional revolutions of thread. As shown in FIG. 1, this is approximately 3 revolutions. Thus, the flute portions 26 and 28 do not extend into the distal thread portion 24.

In order to facilitate the final flow of bone chips out of the flute portions 26 and 28 while the distal thread portion enters the host site, the surgeon can irrigate the site to remove additional bone chips as desired.

It is desirable that the fluted portions 26 and 28 remain filled with bone chips when the implant reaches the designed installation depth. The fact that the flute portions 26 and 28 do not extend into the distal thread portion facilitates ensuring that the flute portions remain filled with bone chips. Because the flute portions 26 and 28 represent a surface which is cut into what is otherwise a substantially cylindrical threaded surface of the implant 10, the surface of the flute portions 26 and 28 would be relatively distant from the host bone in the radial direction relative to axis 16. The distance between the surface of the flute portions 26, 28 and the host bone may lead to insufficient osseointegration, at least in the area adjacent to the surface of the flute portions 26 and 28. By ensuring that the flute portions 26 and 28 remain filled with the cut bone chips, this assists integration of the bone chips with the adjacent host bone leading to integration of the host bone with the surface of the fluted portions 26 and 28. To further assist in integration of host bone adjacent the surface of the flute portions 26 and 28, the surfaces of the flute portions 26 and 28 may be surface treated in any manner which enhances osseointegration. This may include roughening the surface by sand blasting or blasting with glass beads or the like, acid treatment or other surface modification techniques.

The surface of the implant 10 other than the surface of the flute portions 26 and 28 is relatively smooth. The surface along the thread from the crest to the root and any valley between adjacent revolutions must traverse along the host bone as the implant is threaded into the site. In order to minimize damage to the bone, the surface is relatively smooth so as to facilitate the sliding of the surface of the implant relative to the bone. However, once the implant is in place, it is intended that osseointegration occur. As explained above at the outset, much of the effect of the osseointegration is achieved by the helical thread on the exterior surface of the implant. However, micro osseointegration directly at the surface of the implant is also a factor in the stability of the implant and thus the surface is not intended to be so smooth that integration does not occur.

From reference to FIG. 1, it can be appreciated how the implant cuts the aperture in the bone to accommodate the implant and the threaded portion of the implant. The cutting edges 42 and 52 are diagrammatically illustrated in FIG. 1. From reference to FIG. 2, it will be observed that the cutting edges 42 and 52 extend radially outwardly from the axis 16 to the circumference of the implant adjacent the first revolution of the thread of the lead thread portion 20. The thread of the lead thread portion 20, the intermediate thread portion 22 and the distal thread portion 24 comprise the usual crest and root. The lead thread portion 20 comprises three revolutions of the thread. A line indicated at 62 in FIG. 1 joins the tips of the crest of the first three revolutions. This line is referred to herein and in the claims as a crest line. It will be observed that the crest line 62 is not parallel to the longitudinal axis 16. The crest line 62 extends radially outwardly in the distal direction relative to the axis 16, that is, the diameter described by the crest of the thread in the lead thread portion 20 increases in the distal direction from the tip portion. Thus as the implant is rotated, the crest of the thread in the lead portion cuts an increasing diameter until the crest of the thread in the intermediate thread portion 22 is accommodated. Thus, the crest widens the portion of the bone required to accommodate the crest of the thread over the course of the three revolutions of the lead portion of the thread.

From reference to FIG. 2, it will be noted that the end of the cutting edge radially outwardly from the axis 16 is given as the points 43 and 53 of the cutting edges 42 and 52 respectively. Thus, the cutting edges 42 and 52 cut away bone to accommodate the root of the thread out to a diameter defined by the points 43 and 53. This point is shown in FIG. 1 as the point 43. The line 45 illustrated in FIG. 1 is a line parallel to the axis 16 of the implant passing through the outwardly extremity 43 of the cutting edge 42. The line 47 in FIG. 1, is a line drawn through the root of the thread in the intermediate portion 22 and the distal portion 24. The line 45 is displaced from the axis 16 by a distance referred to herein as the cutting edge distance. The line 47 is referred to herein as the root line and the distance of the root line from the axis 16 is referred to as the root distance. The distance between the lines 47 and 45 is shown by the arrow 49.

The distance 49 as illustrated in FIG. 1, illustrates the amount of compression that will be applied to the surface of the bone as the implant passes proximally into the bone. The bone is cut away by the cutting edges 42 and 52 leaving a cylindrical hole. Some further cutting action takes place in the bone by the crest of the thread of the lead portion. As the crest of the thread of the lead portion pass any particular point in the bone, the bone is then compressed a total amount as shown by the distance 49.

The angle of the crest line 62, relative to the axis, establishes a rate of compression, that is, the greater the angle between the crest line 62 and the axis 16, the greater will be the speed of compression for a given rotational speed of the implant 12. The implant may be designed to give any desired rate of compression by including fewer or greater number of revolutions in the lead thread portion.

The distance 49 between the lines 45 and 47 establishes the amount of compression the surface of the bone will be subjected to. That dimension can be altered by altering the radial length of the cutting edges 42 and 52. It will be appreciated by those skilled in this art, that it is desirable to have some compression so as to facilitate osseointegration with the underlying bone. However, too much compression can cause problems including necrosis of the bone cells being compressed. Where an implant is being installed in a less dense bone which is more forgiving, the distance 49 may be larger, perhaps up to as large as ⅓ of the radial distance between the axis 16 and the line 47, that is, the root distance. However, in more dense bone, the amount of compression that may be satisfactory may be much less, perhaps as little as 5%. As those familiar with this area will be well aware, the jaw bone in a human is composed of areas of quite different density. The back portion of the upper jaw is much softer than the front portion of the lower jaw. In relatively softer or less dense bone, a higher permissible compression amount and a higher permissible rate may be acceptable without damaging the bone. In dense bone however, it is likely that there will be a much lower permissible compression amount and a lower permissible compression rate.

The intermediate thread portion 22 commences, as shown in FIG. 1, with the crest of the forth revolution of the thread from the tip portion 18. The line 64 referred to herein as the intermediate portion crest line, joins the tips of the crest of the thread in the intermediate thread portion 22 and in the distal threaded portion 24. The intermediate portion crest line 64 is parallel to the axis 16. This means that there is no additional cutting required to accommodate the crest of the thread in the intermediate and distal thread portions to allow passage of the intermediate thread portion 22 or the distal thread portion 24 in the host bone. Similarly the root line 47 joining the root of the thread in the intermediate thread portion 22 and the distal thread portion 24 is also parallel to the axis 16. These two factors mean that there is no further cutting of the bone at a particular location in the bone once the tip portion 18 and the lead thread portion 20 have passed that particular location.

Osseointegration occurs as the host bone grows around and incorporates the surface of the implant 10. The surface of the entire tip portion 18, the lead thread portion 20, the intermediate thread portion 22 and the distal thread portion 24 will all be in intimate contact with the host bone. As the self tapping implant passes into the bone, there is no excess space or clearance between the implant and the host bone. The only portion of the implant which is not in close contact with the host bone is that portion represented by the surface of the flute portions 26 and 28. For this reason, the circumferential width of the flute portions 26 and 28 should be minimized as much as possible, while providing sufficient space to allow the bone chips created during installation of the implant, to flow along the flute portion and so be removed from the site of the cutting action. As stated above, the passageway defined by the surface of the flute portions 26 and 28 and the surrounding host bone will be filled with bone cuttings generated by the cutting edges. This passageway will remain filled when the implant has been passed in the proximal direction into the bone to the desired depth. Because the flute portions 26 and 28 do not extend into the distal thread portion 24, then there is circumferential contact all the way around the surface of the implant 10 adjacent the distal thread portion 24. The top three revolutions of the thread, that is the thread in the distal thread portion 24, will be in contact with the superior cortex to provide good engagement at the top of the implant. Most stabilization of the implant occurs in the superior cortex and accordingly, it is desirable to have maximum surface area available for integration. In part, this can be achieved by having the flutes 26 and 28 not extend any further distally than necessary for bone chip removal.

The head portion 14 of the implant 10 comprises a generally cylindrical outer surface 70. The diameter of the generally cylindrical surface 70 may be substantially equal to the diameter of the root of the thread in the intermediate and distal threaded portions. The distal end of the cylindrical surface 70 of the head 14 merges with an outwardly flaring tapered surface 72.

In FIG. 1, the head portion 14 is shown in partial section. The head portion 14 comprises an internal bore 80. The internal bore 80 extends generally co-axially with the axis 16. A proximal portion of the bore 80 may be threaded as indicated at 82. The internal thread indicated at 82 of the bore 80 provides a structure for fixing various other structures to the implant 10. During the initial healing stage, a healing cap is used to close the distal end of the bore 80. When the implant is used for the support of a prosthesis, the prosthesis may be attached to an abutment. The abutment will have a thread which is complimentary to the internal thread 82 of the bore 80.

The proximal end of the bore 80 is shown at 84. From FIG. 1 it will be noted that, preferably the distal end 30 of the flute 26 is spaced in the proximal direction from the proximal end 84 of the bore 80. The radial depth of the flute 26 might otherwise encroach upon the wall thickness between the bore 80 and the root of the distal thread portion 24. This in turn might require a bore with a smaller diameter which is not desirable. The radial depth of the flutes 26 and 28 is greatest at the proximal end of the flute and the flute radial depth tapers to zero adjacent the distal end of the flute.

The implant 10 may be made from any material which is suitable for integration into the body. Typically, this may be metals such as titanium or titanium alloys. However, other materials may be used including stainless steel.

In order to install the implant, the site is prepared for installation. A profiling drill is used to make a small dimple in the bone. The dimple is located at the desired location for the axis 16 of the implant. The implant may then be gripped by means of a standard dental tool which grasps the head portion 14 of the implant 10. The head portion 14 of the implant 10 is grasped to prevent any relative rotation between the installation tool and the implant 10. Pressure is then applied to the implant in the proximal direction and the tool is used to rotate the implant. When the implant has been positioned to the desired depth, the tool is removed from the head portion of the implant. Thereafter a healing cap is inserted into the head portion of the implant and the surgical site closed temporarily to permit integration of the implant into the host bone. Typically, integration may take 4 to 6 months. Upon integration of the implant, the site may be opened at the distal end and a prosthesis attached to the implant by means of the thread 82 in the internal bore 80.

While the invention has been discussed in the context of the preferred embodiment, it will be apparent that various modifications may be made.

We claim:

1. A dental implant comprising a body portion and a head portion, said body portion comprising a tip portion remote from said head portion, said body portion of said implant having an external thread including 1) a lead thread portion adjacent said tip portion, 2) an intermediate thread portion adjacent said lead thread portion and 3) a distal thread portion, adjacent said head portion, wherein said thread of said lead thread portion, said intermediate thread portion and said distal thread portion comprises a cutting edge so that said implant is self-tapping said dental implant further comprising a central bore within said head portion and an internal thread within said bore for receiving a dental prosthesis, and wherein said tip portion comprises at least one cutting edge for cutting bone to form a bore as said implant is rotated, said body portion comprising at least one flute, said flute having a first end adjacent said at least one cutting edge of said tip portion for assisting removal of bone cuttings from said cutting edge, said body portion having a generally longitudinal axis and said cutting edge of said tip portion commencing at said axis and extending radially outwardly from said axis so that upon rotation of said implant in a patient's jaw, said implant is self-drilling and self-tapping.

2. The dental implant of claim 1 wherein said body portion comprises an outer surface and said at least one flute extends along said outer surface of said body portion in a direction substantially parallel to said axis.

3. The dental implant of claim 2 wherein said implant comprises two said cutting edges and two said flutes.

4. The dental implant of claim 2 wherein said flute extends from said tip portion along said lead thread portion and said intermediate thread portion of said body portion.

5. The dental implant of claim 4 wherein said flute has a distal end and said distal end is adjacent a proximal end of said distal thread portion.

6. The dental implant of claim 4 wherein said flute has a flute surface and said surface of said flute is roughened to assist in osseointegration.

7. The dental implant of claim 6 wherein the surface of said lead thread portion and the surface of said intermediate thread portion of said body portion are smooth.

8. The dental implant of claim 4 wherein said lead thread portion comprises at least three revolutions.

9. The dental implant of claim 8 wherein said external thread has a crest and a crest line joining the crest of said three revolutions of said lead thread portion extends radially outwardly, distally, relative to said axis.

10. The dental implant of claim 9 wherein a crest line joining the crest of the thread of said intermediate thread portion and said distal thread portion is substantially parallel to said axis.

11. The dental implant of claim 10 wherein said external thread has a root and a root line extending through the root of the thread of said intermediate portion and said distal portion is parallel to said axis and is displaced from said axis a root distance and wherein said at least one cutting edge extends from said axis radially outwardly to a respective cutting edge end and said cutting edge end is displaced from said axis, a cutting edge distance and wherein said root distance is greater than said cutting edge distance.

12. The dental implant of claim 11 wherein the difference between said root distance and said cutting edge distance is not greater than one third of said root distance.

13. The dental implant of claim 12 wherein said difference is not greater than five percent (5%) of said root distance.

14. The dental implant of claim 1 wherein said implant comprises at least two said cutting edges and at least two said flutes.

15. A dental implant comprising a body portion and a head portion, said body portion comprising a tip portion remote from said head portion, said body portion of said implant having an external thread including 1) a lead thread portion adjacent said tip portion, 2) an intermediate thread portion adjacent said lead thread portion and 3) a distal thread portion, adjacent said head portion, wherein said thread of said lead thread portion, said intermediate thread portion and said distal thread portion comprises a cutting edge so that said implant is self-tapping said dental implant further comprising a central bore within said head portion and an internal thread within said bore for receiving a dental prosthesis, and wherein said tip portion comprises at least one cutting edge for cutting bone to form a bore as said implant is rotated, said body portion comprising at least one flute, said flute having a first end adjacent said at least one cutting edge of said tip portion for assisting removal of bone cuttings from said cutting edge, said body portion having a generally longitudinal axis and said cutting edge of said tip portion commencing at said axis and extending radially outwardly from said axis so that upon rotation of said implant in a patient's jaw, said implant is self-drilling and self-tapping, and wherein said body portion comprises an outer surface and said at least one flute extends along said outer surface of said body portion in a direction substantially parallel to said axis, and wherein said external thread has a root and a root line extending through the root of the thread of said intermediate portion and said distal portion is parallel to said axis and is displaced from said axis a root distance and wherein said at least one cutting edge extends from said axis radially outwardly to a respective cutting edge end and said cutting edge end is displaced from said axis, a cutting edge distance and wherein said root distance is greater than said cutting edge distance.

16. The dental implant of claim 15 wherein said flute extends from said tip portion along said lead thread portion and said intermediate thread portion of said body portion.

17. The dental implant of claim 16 wherein said flute has a distal end and said distal end is adjacent a proximal end of said distal thread portion.

18. The dental implant of claim 17 wherein the difference between said root distance and said cutting edge distance is not greater than one third of said root distance.

19. The dental implant of claim 18 wherein said difference is not greater than five percent (5%) of said root distance.

* * * * *